(12) United States Patent
Martin et al.

(10) Patent No.: US 6,962,434 B2
(45) Date of Patent: Nov. 8, 2005

(54) LINER WEAR DETECTION

(75) Inventors: Robert O. Martin, Edmond, OK (US); Joe Bert Maker, Guthrie, OK (US); Lonnie G. Hewell, Guthrie, OK (US)

(73) Assignee: Kerr-McGee Chemical, LLC, Oklahoma City, OK (US)

( * ) Notice: Subject to any disclaimer, the term of this patent is extended or adjusted under 35 U.S.C. 154(b) by 0 days.

(21) Appl. No.: 10/670,586

(22) Filed: Sep. 25, 2003

(65) Prior Publication Data

US 2005/0069016 A1 Mar. 31, 2005

(51) Int. Cl.[7] .......................... G01N 17/00; G01K 7/02
(52) U.S. Cl. ............................ 374/7; 374/179; 374/57; 374/102
(58) Field of Search .................... 374/4–7, 29, 45, 374/57, 102, 208, 147, 148, 142, 179; 702/33–35, 702/40, 51

(56) References Cited

U.S. PATENT DOCUMENTS

| 255,427 A | 3/1882 | Forman |
| 896,762 A | 8/1908 | Schenck |
| 1,140,720 A | 5/1915 | Simons |
| 1,208,049 A | 12/1916 | Tillman |
| 1,992,960 A | 3/1935 | Miller et al. ................. 285/106 |
| 3,360,977 A * | 1/1968 | Herman ............................. 73/9 |
| 4,234,274 A | 11/1980 | Hoshall ........................ 406/93 |
| 4,301,651 A | 11/1981 | Cocchiara et al. ............. 60/282 |
| 4,535,326 A * | 8/1985 | Mullins et al. .............. 340/679 |
| 4,536,105 A | 8/1985 | Bungert ....................... 406/183 |
| 4,554,721 A | 11/1985 | Carty et al. ..................... 29/416 |
| 4,646,001 A * | 2/1987 | Baldwin et al. ............. 324/700 |
| 4,684,155 A | 8/1987 | Davis .......................... 285/16 |
| 4,697,456 A * | 10/1987 | Maser .......................... 73/592 |
| 4,900,345 A | 2/1990 | Le Jeune ...................... 55/337 |
| 4,971,179 A * | 11/1990 | Gebhardt et al. ............. 188/33 |
| 5,072,622 A * | 12/1991 | Roach et al. ............. 73/40.5 R |
| 5,301,984 A | 4/1994 | Farris .......................... 285/55 |
| 5,399,019 A * | 3/1995 | Kourtides ................... 374/208 |
| 5,559,286 A * | 9/1996 | White et al. .................. 73/129 |
| 5,573,282 A | 11/1996 | Egner et al. .................... 285/55 |
| 5,637,794 A * | 6/1997 | Hanisko ....................... 73/121 |
| 5,909,171 A * | 6/1999 | Kyrtsos ...................... 340/454 |
| 6,002,564 A * | 12/1999 | Ohtsuchi ................... 361/93.1 |
| 6,004,639 A | 12/1999 | Quigley et al. |
| 6,080,982 A * | 6/2000 | Cohen ................... 250/227.11 |
| 6,121,617 A * | 9/2000 | Hirayama et al. .......... 250/343 |
| 6,360,850 B1 * | 3/2002 | Odisho et al. .......... 188/1.11 L |
| 6,422,608 B1 | 7/2002 | Lee et al. ..................... 285/179 |
| 6,467,812 B1 | 10/2002 | Klemm et al. ................. 285/55 |
| 6,686,752 B1 | 2/2004 | Heumann et al. ........... 324/700 |
| 2001/0021360 A1 | 9/2001 | Yuill et al. |
| 2004/0098233 A1 * | 5/2004 | Renner ....................... 702/189 |

FOREIGN PATENT DOCUMENTS

| EP | 0058653 | 8/1982 | |
| FR | 2319880 A * | 4/1997 | .......... B60K 35/00 |
| GB | 2207473 | 2/1989 | |
| WO | WO 00/61472 | 10/2000 | |

* cited by examiner

*Primary Examiner*—Gail Verbitsky
(74) *Attorney, Agent, or Firm*—Law Office of Stanley K. Hill, PLC

(57) ABSTRACT

Methods and apparatus for detecting wear in a liner. In one embodiment of the present invention, an electrically conductive wire is placed on or near the outside surface of the liner and the electrical resistance in the electrically conductive wire is measured to determine whether the wire has worn through. In another embodiment of the present invention, the temperature measured by a temperature measuring device, such as a thermocouple, is monitored over time to estimate wear in the liner.

8 Claims, 12 Drawing Sheets

LINER WEAR DETECTION

FIELD OF THE INVENTION

The present invention generally relates to apparatus for changing the direction of a fluid flow, especially of highly abrasive fluid flows in lined piping systems. In preferred embodiments, the present invention relates to changing the direction of flow of such fluids in a small space with a smaller pressure loss or pressure drop than is found when using conventional technology to change the direction of a fluid flow.

BACKGROUND AND SUMMARY OF THE INVENTION

In any enclosed system containing a flowing fluid, such as a piping system, there is frequently a need to make directional changes in the fluid flow. Typically, standard piping elbows, also referred to as bends, are used. However, circumstances frequently exist that impose constraints and preclude the use of standard piping elbows. These circumstances include the conveying of high temperature fluids, corrosive fluid streams, or abrasive fluid streams such as those that are particulate-laden fluid streams. When these conditions exist, a typical solution to changing the fluid flow direction often involves using larger size (that is, greater diameter) piping elements lined with an appropriate refractory, corrosion-resistant, or abrasion-resistant lining.

An increase in the piping diameter requires an accompanying increase in the turning radius of any needed bends. The increase in turning radius in turn increases the space requirements for installing an elbow or bend needed to make a change in the fluid flow direction. Utilizing an elbow or bend with too small of a turning radius typically causes an undesirable pressure loss.

As related in a commonly-assigned application filed concurrently with the present application, the inventors have addressed these deficiencies by providing a piping elbow capable of facilitating a fluid flow direction change in a smaller space than conventional piping elbows, without causing the larger pressure losses found when using conventional elbows in the equivalent space. These piping elbows comprise a substantially-cylindrical body having a first end, a second end, and a substantially-constant inside diameter; a tangential inlet attached to the body near the first end of the body and having an inside diameter smaller than the inside diameter of the body; and a tangential outlet attached to the body near the second end of the body and having an inside diameter smaller than the inside diameter of the body. Typically, fluid flows linearly through the tangential inlet and enters the body. Inside the body, linear motion of the fluid is converted into a rotational or spiral motion. The fluid in the body continues its spiral motion as it also moves axially through the body toward the tangential outlet. The fluid exits the body through the tangential outlet. Upon exiting through the tangential outlet, rotational or spiral motion of the fluid in the body is converted back into linear motion.

In a preferred embodiment, the piping elbows comprise two substantially-identical components attached to each other. In another preferred embodiment, the two substantially-identical components are removably attached to each other so that the tangential inlet/outlet on the first component can be oriented at any desired angle with respect to the tangential inlet/outlet on the second component.

Together with the development of the described piping elbows, and as related in a further commonly-assigned application filed concurrent with the present application, the inventors have additionally conceived a liner for use with the piping elbows. In one embodiment, the liner comprises a body liner, a tangential inlet liner, and a tangential outlet liner. In a preferred embodiment, the tangential inlet liner and the tangential outlet liner are each removably inserted into a cavity in the body liner. In another embodiment, the body section liner comprises two substantially-identical body section liners.

The present application, in a preferred embodiment, concerns methods and apparatus for detecting wear in such liners, though it will be appreciated that the inventive methods and apparatus are more broadly applicable to the whole of lined vessels generally (and "vessels" here should be taken as referring to any structure in or through which a fluid, especially an abrasive fluid, moves). In one embodiment, an electrically conductive wire is placed on or near the outside surface of the liner (relative to the fluid flow) and the electrical resistance in the electrically conductive wire is measured to determine whether the wire has worn through. In another embodiment, the temperature measured by a temperature measuring device, such as a thermocouple, is monitored over time to estimate wear in the liner.

DESCRIPTION OF THE DRAWINGS

The present invention is illustrated by way of example in the following drawings in which like references indicate similar elements. The following drawings disclose various embodiments of the present invention for purposes of illustration only and are not intended to limit the scope of the invention.

DETAILED DESCRIPTION OF PREFERRED EMBODIMENTS OF THE INVENTION

Figure 1:
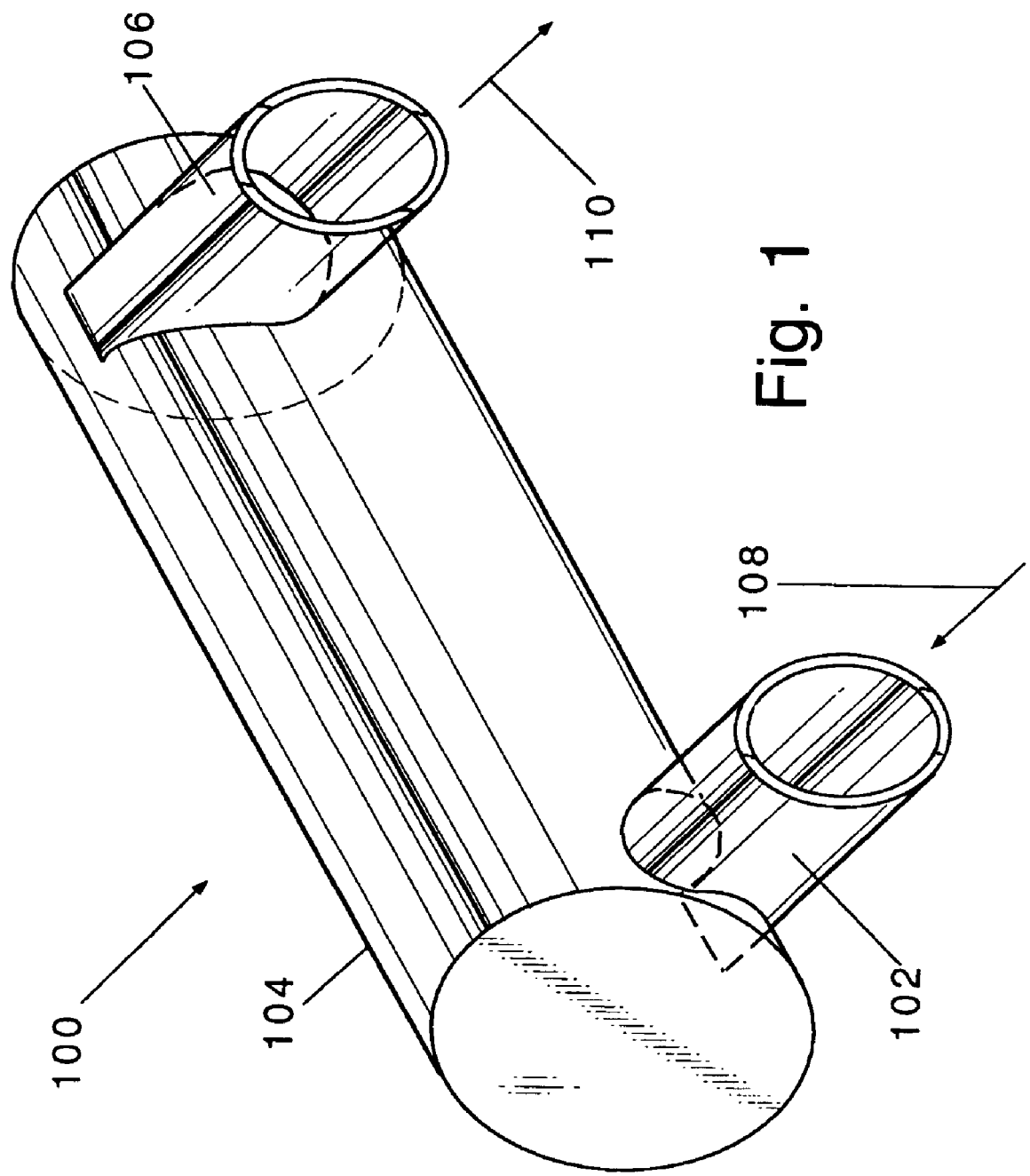
FIG. 1 shows a piping elbow having a tangential inlet and tangential outlet that are axially oriented in substantially opposite directions.

In the following detailed description of preferred embodiments of the present invention, reference is made to the accompanying Drawings, which form a part hereof, and in which are shown by way of illustration specific embodiments and contexts in which the liner wear detection methods and apparatus of the present invention may be practiced. It should be understood that other embodiments may be utilized and changes may be made without departing from the scope of the present invention.

The piping elbows to which the present inventive methods and apparatus are applied in preferred embodiments comprise a substantially-cylindrical body having a first end and a second end and having a substantially-constant diameter; a tangential inlet attached to the body section near the first end of the body section and having a diameter smaller than the diameter of the body section; and a tangential outlet attached to the body section near the second end of the body section and having a diameter smaller than the diameter of the body section. Unless specified otherwise herein, the word "diameter" will refer to the inside diameter of an article.

For purposes of the present specification the first end of the body section may from time to time also be referred to as the "top" of the body, and thus the "top" of the piping elbow, while the second end may be referred to as the "bottom" of the body and the "bottom" of the piping elbow. While the words "top" and "bottom" may be used as a matter of convenience in the course of the present description to indicate specific ends of the body and piping elbow, the use of the words "top" and "bottom" rather than "first end" or "second end" should not be taken to indicate or imply that the piping elbows in which the liner detection methods and apparatus find application necessarily are vertically-oriented or have a "top" or "bottom" end—the ends may be at the same elevation.

In a piping elbow of the type shown in the drawings, fluid flows linearly through the tangential inlet and enters the body. Inside the body, essentially linear motion of the fluid is converted into a rotational or spiral motion. The fluid in the body continues its spiral motion as it also moves axially through the body section, toward the tangential outlet. The fluid exits the body through the tangential outlet. Upon existing through the tangential outlet, rotational or spiral motion of the fluid in the body is converted back into linear motion.

FIG. 1 shows an example of such a piping elbow 100. The piping elbow 100 comprises a tangential inlet 102, a body 104, and a tangential outlet 106. In a typical operation of the piping elbow 100, fluid flows essentially linearly through the tangential inlet 102, as indicated by the arrow 108, and enters the body 104. Upon entering the body 104, linear motion of the fluid flow is converted to a spiral motion as the fluid moves axially from the tangential inlet 102 toward the tangential outlet 106. Upon reaching the tangential outlet 106, spiral motion is translated back to linear motion as the fluid exits the body 104 as indicated by the arrow 110.

Figure 2:
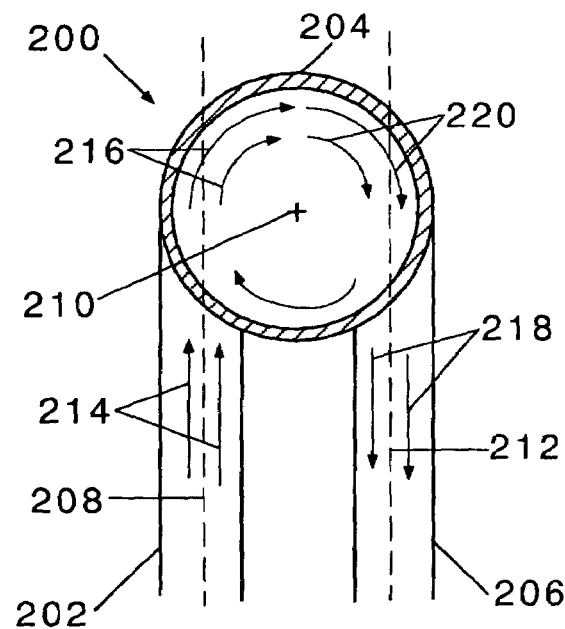
FIG. 2 shows a top-down view of the piping elbow of FIG. 1.

In order to facilitate the spiral motion of the fluid in the body, inlets and outlets according to the present invention are both smaller in diameter than the body. By tangential it is meant that the axis of the inlet (or outlet) does not pass through the axis of the body. The tangential inlet and tangential outlet can also be thought of as being off-center in relation to the body. The tangential nature of the inlet and outlet are more clearly illustrated in FIG. 2. FIG. 2 shows a top-down view of a piping elbow 200 similar to the piping elbow 100 illustrated in FIG. 1. The piping elbow 200 comprises a tangential inlet 202, a body 204, and a tangential outlet 206. As shown in FIG. 2, the axis 208 of the tangential inlet 202 does not intersect with the axis 210 of the body 204. If a tangential inlet were centered with respect to a body, then the axis of the tangential inlet would intersect the axis of the body. Similarly, the axis 212 of the tangential outlet 206 does not intersect with the axis 210 of the body 204.

Fluid enters the body 204 through the tangential inlet 202 as indicated by the arrows 214. Inside the body 204, fluid travels toward the tangential outlet in a spiral motion as indicated by the arrows 216. Upon reaching the tangential outlet 206, fluid exits the body as indicated by the arrows 218.

The tangential inlet and tangential outlet are both smaller in diameter than the body. For many applications, the diameter of the tangential inlet will be about the same size as the diameter of the tangential outlet. Preferably, the diameter of the body is at least about 1.5 times as large as the diameter of the tangential inlet and the diameter of the tangential outlet. More preferably, the diameter of the body is at least about 2 times as large as the diameter of the tangential inlet and the diameter of the tangential outlet. Preferably, the diameter of the body section is no more than about 3 times as large as the diameter of the tangential inlet and the diameter of the tangential outlet.

The tangential inlet and tangential outlet may be axially-oriented in any direction relative to each other. For example, in FIG. 2 the direction of the fluid flow in the tangential inlet 202 is in the opposite direction of the fluid flow in the tangential outlet 206. That is, the direction of the fluid flow in the tangential inlet 202 is about 180 degrees in relation to the fluid flow in the tangential outlet 206. Thus, the tangential inlet 202 is axially-oriented in the opposite direction of the tangential outlet 206. A piping elbow having a tangential inlet and a tangential outlet axially-oriented in substantially the opposite direction can be advantageously utilized when the elbow is part of a piping system serving as a return, such as when a product of a production system is returned or recycled back into the production system. The tangential inlet can be at the same elevation or a different elevation than the tangential outlet depending on the needs in any application.

To facilitate the exit of the fluid flow through the tangential outlet, the tangential outlet should be positioned on the opposite side of the body section's axis than the tangential inlet when the inlet and outlet are axially-oriented in the opposite direction. For example, in the top-down view of piping elbow 200 shown in FIG. 2 the axis 208 of the tangential inlet 202 appears to the left of the body's axis 210 and the axis 212 of the tangential outlet 206 appears to the right of the body's axis 210. The positioning of the tangential inlet 202 to the left of the body's axis 210 causes the fluid flow in the piping elbow 200 to spiral in a clockwise motion as indicated by the arrows 216. As the fluid flow continues to spiral it moves axially through the body 204 from the tangential inlet 202 to the tangential outlet 206. As the fluid flow reaches the tangential outlet 206, the fluid flow is moving in the direction needed to exit through the tangential outlet 206 as indicated by the arrows 220 and 218. The tangential inlet 202 and the tangential outlet 206 can in this circumstance be described as "rotationally aligned." If on the other hand, the tangential outlet 206 had been positioned directly underneath the tangential inlet 202 such that both axis 208 and 212 were positioned to the left of the body's axis 210, then as the fluid flow reached the tangential outlet 206 it would not be moving in the same direction as needed to exit the tangential outlet 206.

Figure 3:
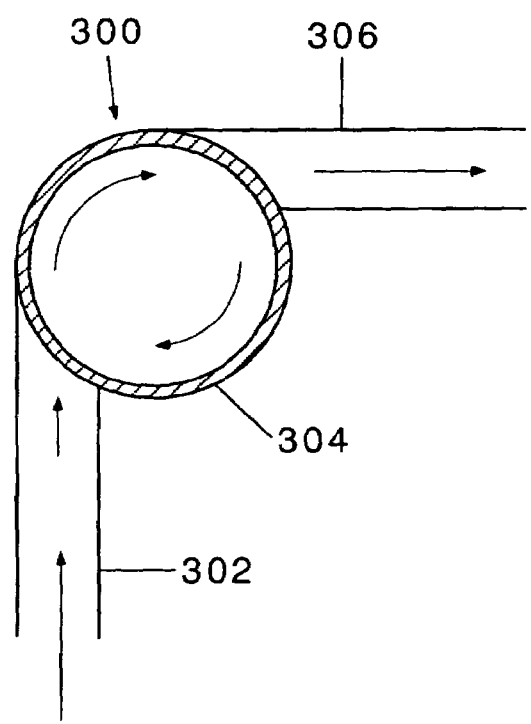
FIG. 3 shows a top-down view of a piping elbow with a tangential inlet and tangential outlet that are axially oriented at about 90 degrees to each other.
Figure 4:
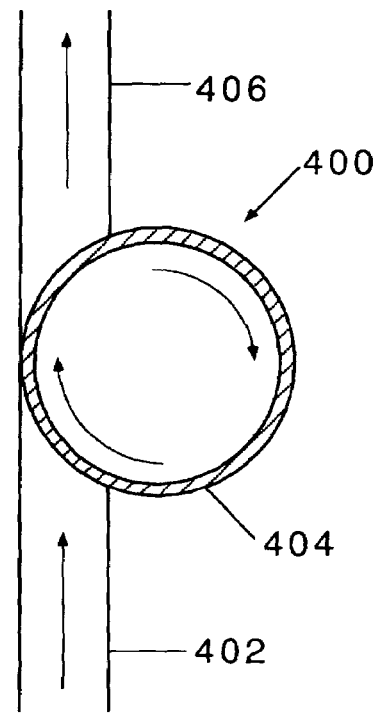
FIG. 4 shows a top-down view of a piping elbow with a tangential inlet and tangential outlet that are axially oriented in substantially the same direction.

FIG. 3 and FIG. 4 illustrate other examples of piping elbows wherein the tangential inlet and tangential outlet are rotationally aligned. In FIG. 3, the piping elbow 300 comprises a tangential inlet 302, a body 304, and a tangential outlet 306, wherein the tangential inlet 302 and the tangential outlet 306 are rotationally aligned and are axially oriented at about 90 degrees to each other. In FIG. 4, the piping elbow 400 comprises a tangential inlet 402, a body 404, and a tangential outlet 406, wherein the tangential inlet 402 and the tangential outlet 406 are rotationally aligned and are axially oriented in substantially the same direction.

Figure 5:
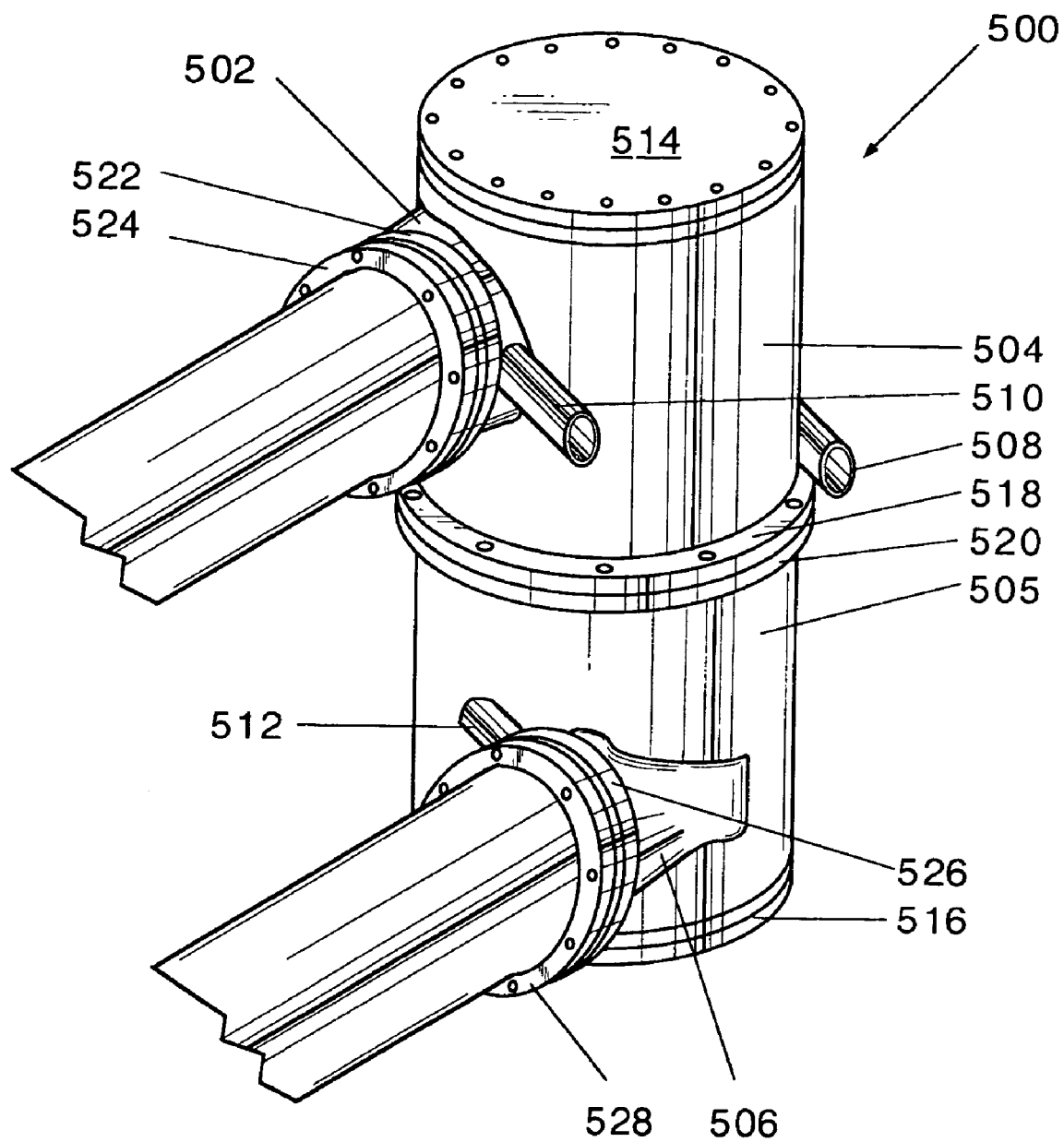
FIG. 5 shows a piping elbow of the type shown in FIG. 1 but which is comprised of two substantially identical component sections, providing a tangential inlet and tangential outlet that are axially oriented in substantially-opposite directions.

Piping elbows as illustrated in FIGS. 1–4 can be manufactured as one solid piece (as shown in FIG. 1) or, more preferably, can be manufactured in parts that can be assembled to form the piping elbow. In FIG. 5, the piping elbow 500 comprises a tangential inlet 502, a body assembled from two body sections 504 and 505, and a tangential outlet 506, wherein the tangential inlet 502 and the tangential outlet 506 are rotationally aligned and are axially oriented in substantially the opposite direction. Preferably, tangential inlet 502 and first body section 504 comprise a single continuous piece and tangential outlet 506 and second body section 505 comprise a second single continuous piece. The body of the piping elbow 500 is assembled by attaching the flange 518 of the first body section 504 to the flange 520 of the second body section 505 in conventional manner. The top 514 of the first body section 504 is attached to the first body section 504 and the bottom 516 of the second body section 505 is attached to the second body section 505. The first body section 504 and the second body section 505 can be separated after use so that the interior of the body can be inspected and cleaned, if necessary. Similarly, the top 514 and bottom 516 are removable so that the interior of the body can be inspected and cleaned as needed. Additionally, the piping elbow 500 can be removed from the rest of the piping system to facilitate inspection, cleaning, repair, replacement, etc. by separating flange 522 from flange 524 and separating flange 526 from flange 528.

Alternate configurations are also possible. For example, the top 514 and/or bottom 516 of body sections 504 and 505 respectively may be permanently attached instead of removably attached as described above. The top 514 and/or bottom 516 may be permanently attached in any way suitable for the particular application. For example, the top 514 and/or bottom 516 can be manufactured as one continuous component along with body-section 504 and/or body-section 505.

Most preferably, for simplicity and ease of manufacture the body-sections 504 and 505 are substantially identical to one another, and removably attached via flanges 518 and 520 in a reverse mirror-image relationship. Thus, in FIG. 5, the piping elbow 500 can be separated into two substantially-identical components by separating flange 518 from flange 520. The first substantially-identical component comprises body section 504, tangential inlet 502, and top 514. The second substantially-identical component comprises body section 505, tangential outlet 506, and bottom 516.

Figure 6:
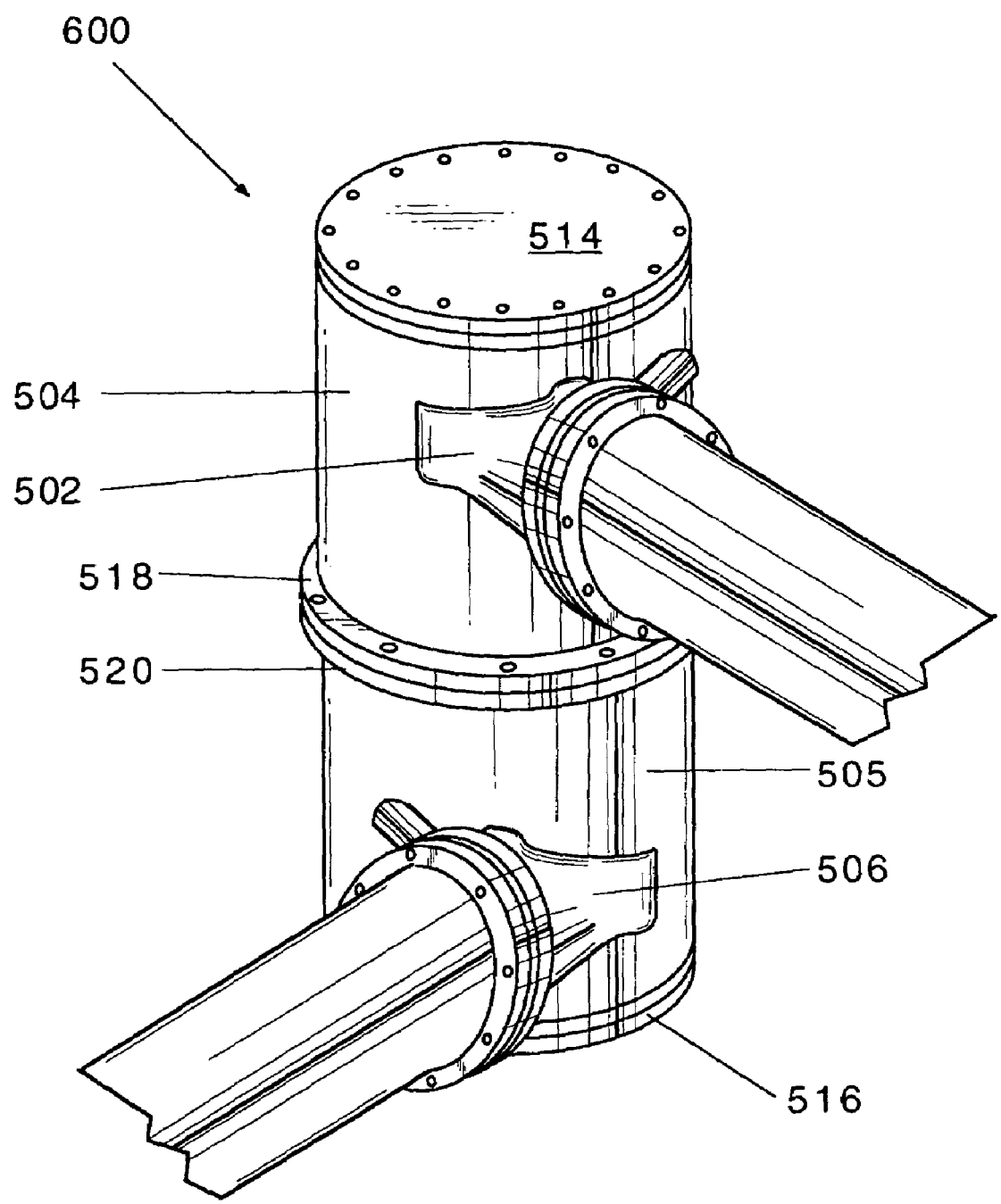
FIG. 6 shows the piping elbow of FIG. 5, wherein the two component sections have been attached so that the tangential inlet and tangential outlet are axially oriented at about 90 degrees to each other.
Figure 7:
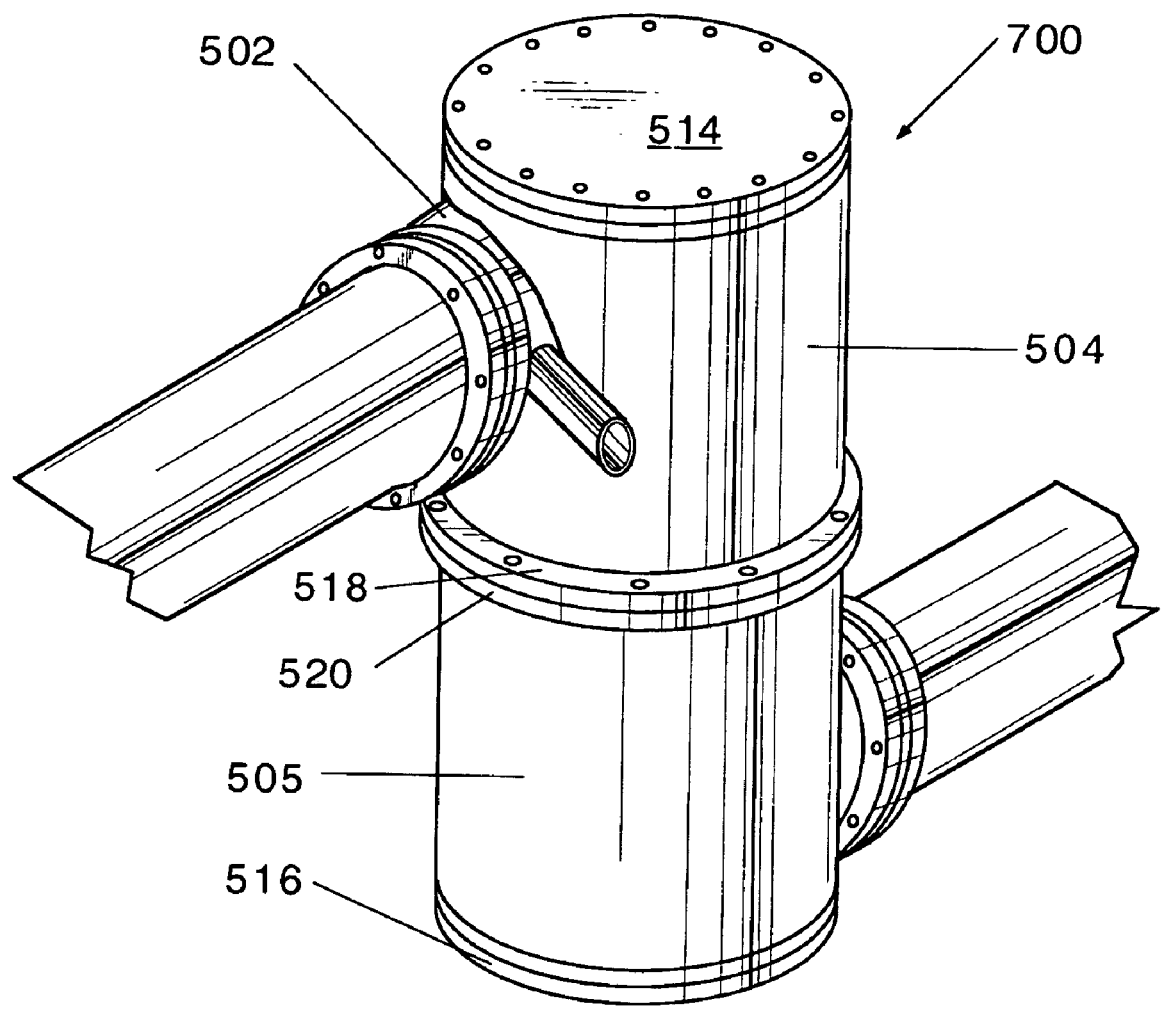
FIG. 7 shows the piping elbow of FIG. 5, wherein the two component sections have been attached to provide a tangential inlet and tangential outlet that are axially oriented in substantially the same direction.

FIGS. 5–7 illustrate another advantage of piping elbows that comprise two substantially-identical components. That is, the bottom component can be oriented at a selected degree relative to the top component to provide a desired redirection of the fluid flow in moving from the tangential inlet through the body and out through the tangential outlet. For example, FIG. 6 shows the piping elbow 500 of FIG. 5 with the bottom component at an angle of approximately 90 degrees relative to the top component. That is, piping elbow 600 of FIG. 6 comprises the exact same components of piping elbow 500 except that the bottom component is rotated approximately 90 degrees. Similarly, FIG. 7 shows piping elbow 700 comprising the exact same components of piping elbow 500 except that the bottom component is rotated approximately 180 degrees.

Piping elbows as illustrated and described above may include cooling jackets. Cooling jackets are known in the art for cooling materials inside vessels or piping systems. For example, piping elbow 500 comprises a cooling jacket. As shown best in FIG. 5, both the first body section 504 and second body section 505 of the piping elbow 500 comprise a cooling jacket that includes a water inlet and water outlet, in the case of body section 504 being inlet 508 and outlet 510. The water inlet for body section 505, which is symmetric to water inlet 508 and in the same relationship to outlet 512 as inlet 508 is to outlet 510, is not shown.

Piping elbows to which the present inventive methods and apparatus apply additionally comprise a liner made of material suitable to the environment in which the piping elbow will be used, and especially being suitable for use with abrasive fluids. For example, ceramic liners can be advantageously utilized with piping elbows such as piping elbow 500 of FIG. 5 in a $TiO_2$ production process. After the burner section or oxidation section in a $TiO_2$ production process, the $TiO_2$ is carried by the process gases through a cooling section. The cooling section is both a highly abrasive environment and a high temperature environment. It is not unusual for the temperature of the fluid stream comprising $TiO_2$ and process gases to vary between 400° F. (204.44° C.) and 1400° F. (760° C.). Piping elbows with ceramic liners can be advantageously utilized in this cooling section of a $TiO_2$ production process.

In one embodiment, the liners used will comprise a body liner, a tangential inlet liner, and a tangential outlet liner. In a preferred embodiment, the tangential inlet liner and the tangential outlet liner have substantially the same shape. That is, the tangential inlet liner and the tangential outlet liner are substantially identical. The body liner may comprise a single continuous component or may comprise multiple section liners. In a preferred embodiment, the body liner comprises two substantially-identical body section liners. Each of the two substantially-identical body section liners has a cylindrical shape that is open at one end and closed at the other end. The closed end can be closed by removably attaching an end to the body section liner or by manufacturing the body section liner as one continuous piece having a closed end. In one embodiment, at least one body section liner has a removably attached end functioning as either a top or bottom of the liner, which can be removed to inspect or clean the inside of the body section liner.

Figure 8:
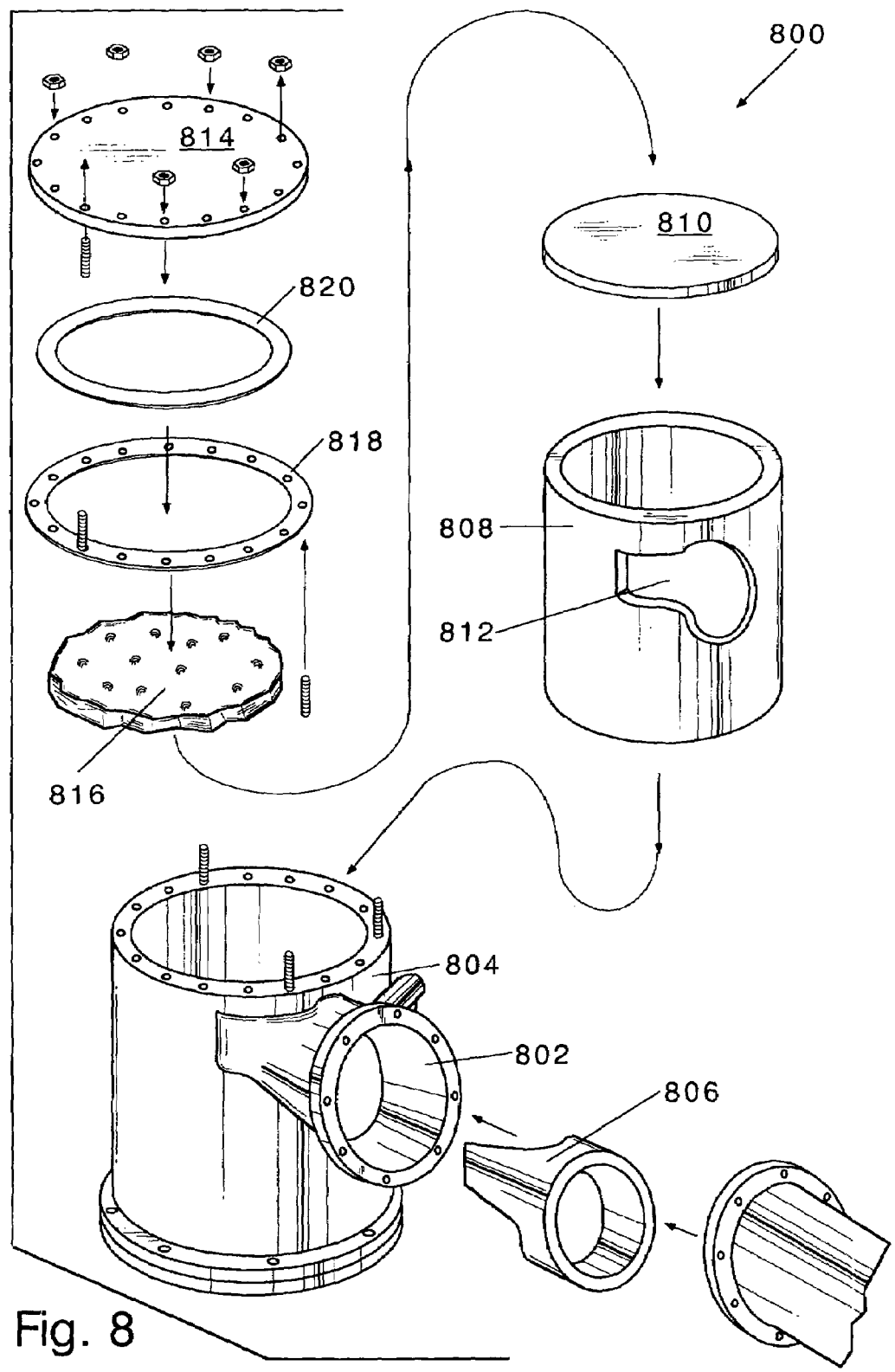
FIG. 8 shows an exploded view of one of two substantially-identical piping constructs reflected in FIGS. 5 through 7.
Figure 9:
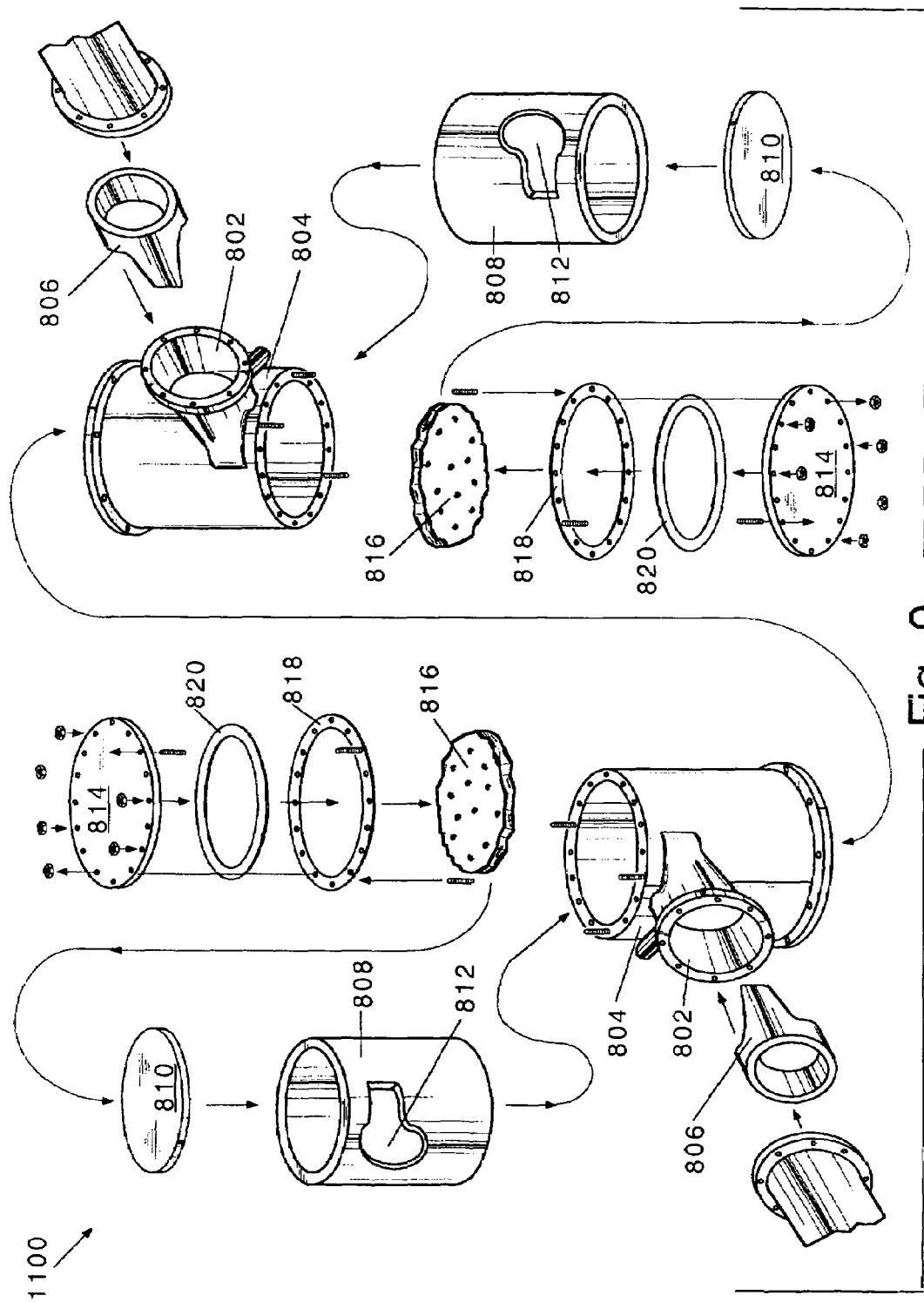
FIG. 9 shows an exploded view of two piping constructs of FIG. 8 removably attached to each other.

FIG. 8 shows an exploded view of a component 800, which is one of two substantially-identical components that can be removably attached to each other to form a piping elbow as described above. The component 800 is similar to the top component shown in FIG. 5 and comprises a body section 804, a tangential inlet 802, and a top 814. It should be noted that if component 800 were used as a bottom component instead of a top component, then the tangential inlet 802 would function as a tangential outlet. Component 800 further comprises a tangential inlet liner 806, a body section liner 808, and a top liner 810. During the process of putting component 800 together, the body section liner 808 is inserted into the body section 804 and then the tangential inlet liner 806 is inserted into the tangential inlet 802 such that the tangential inlet liner 806 fits into the cavity 812 in the body section liner 808. The tangential inlet liner 806 and the cavity 812 are shaped such that the edges of the tangential inlet liner 806 line up with the edges of the cavity 812. Thus, the shape of the cavity 812 in the body section liner 808 is substantially identical to the shape of the inserted end of the tangential inlet liner 806. The construction of component 800 is finished by placing the top liner 810 onto the body section liner 808, placing insulation 816 onto the top liner 810, placing a gasket 818 on top of the body section 804, applying a gasket sealer 820 on top of the gasket 818, and then attaching the top 814 to the body section 804. In FIG. 8, the top 814 is removably attached to the body section 804 by bolting the top 814 to the body section 804. FIG. 9 shows an exploded view of two components 800 removably attached to each other to form a piping elbow.

Figure 10:
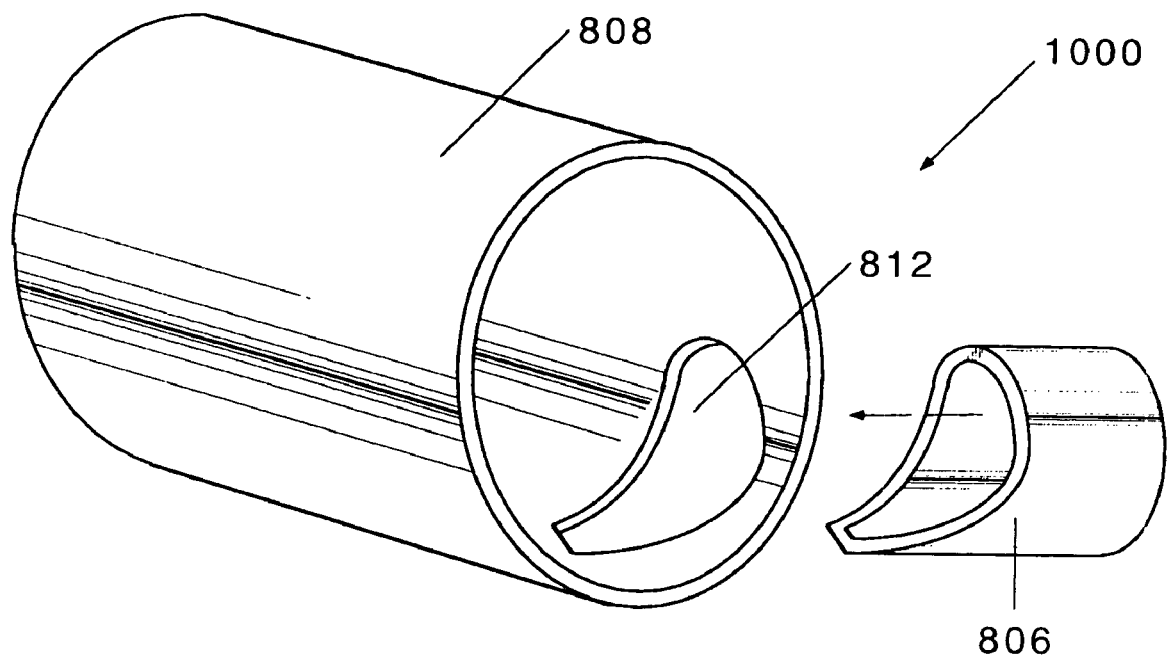
FIG. 10 shows another view of the body section liner and tangential inlet liner shown in FIGS. 8 and 9.
Figure 11:
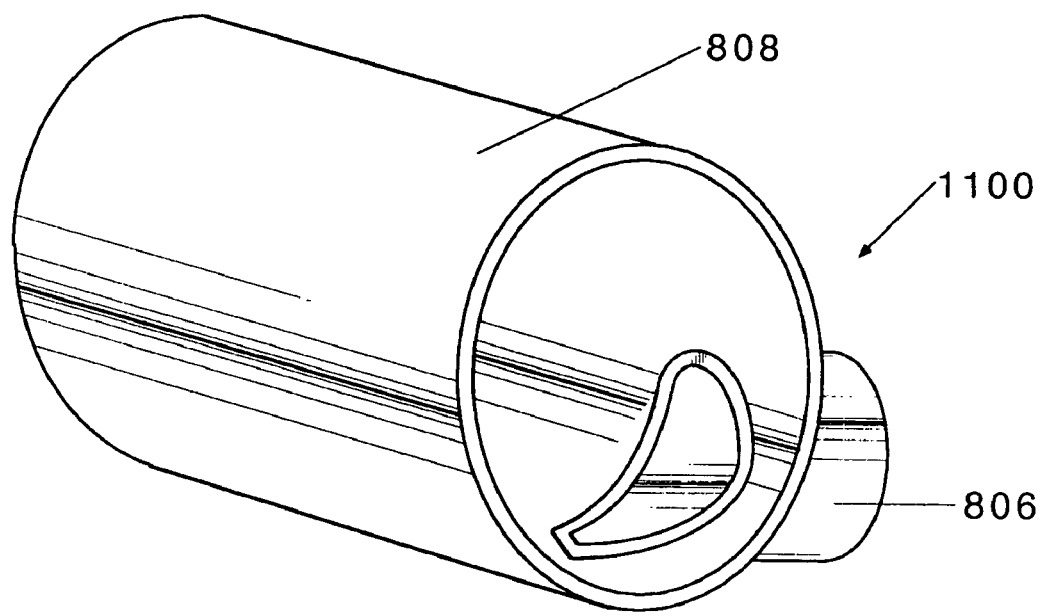
FIG. 11 shows the tangential inlet liner of FIGS. 8, 9, and 10 inserted into the cavity of the body section liner of FIGS. 8, 9, and 10.

FIGS. 10–11 illustrate how tangential inlet liners and tangential outlet liners fit into a cavity of either a body liner or a body section liner to form a liner joint. FIG. 10 shows the tangential inlet liner 806, the body section liner 808, and the cavity 812 of FIGS. 8 and 9. As shown in FIG. 10, the shape of the inserted end of the tangential inlet 806 is substantially identical to the shape of the cavity 812 in the body section liner 808. FIG. 11 shows the tangential inlet liner 806 inserted into the cavity 812 of the body section liner 808 forming a liner component 1100 suitable for use in a first component of a piping elbow. The point at which an inlet or outlet is inserted into the cavity of a body liner or body section liner may be referred to herein as a liner joint.

Figure 12:
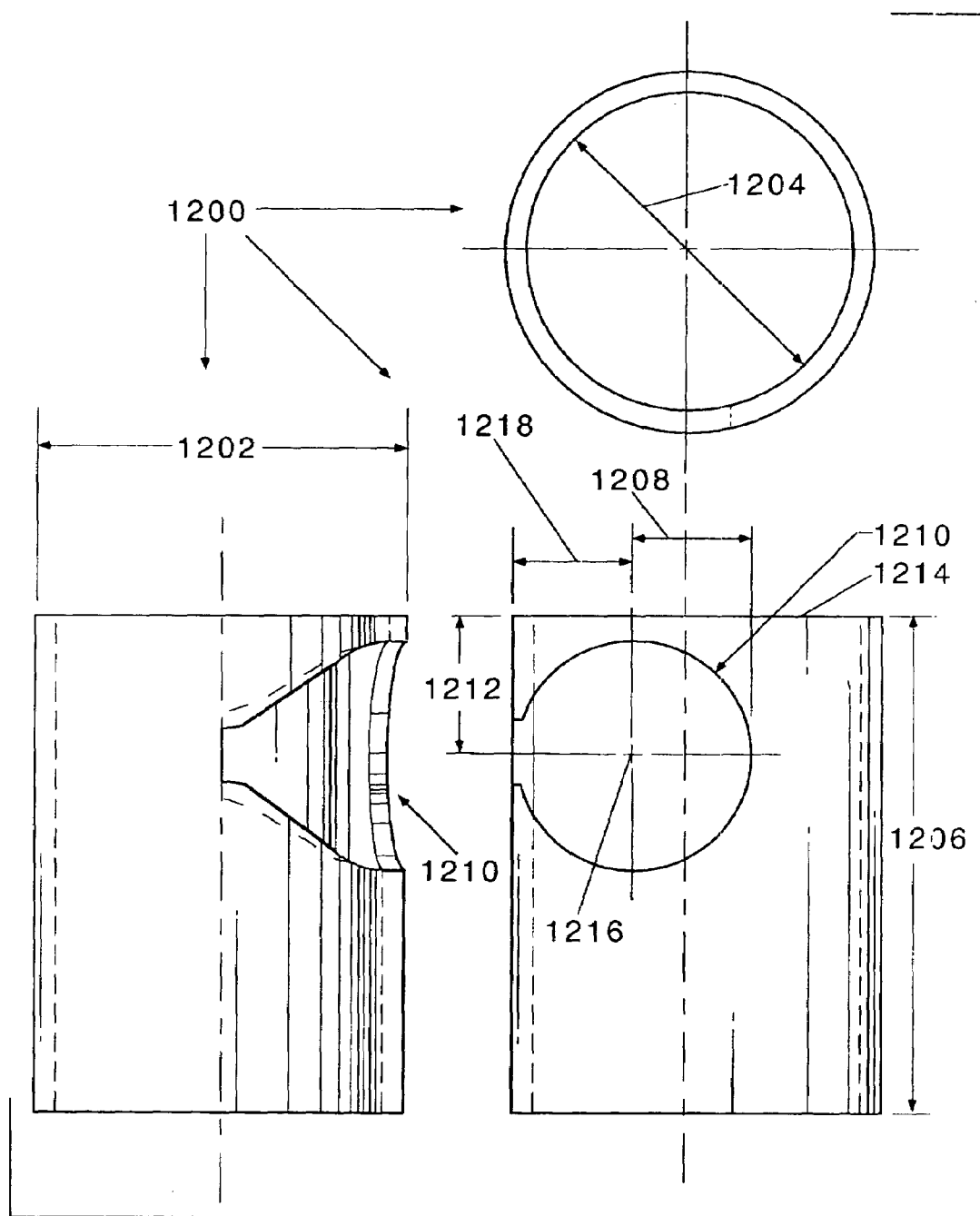
FIG. 12 shows a schematic of the body section liner of FIG. 10.

The cavity in a body liner or body section liner can be created by removing a plug from a cylindrical piece of lining material. Ceramic pieces of lining material may be purchased from Ceramic Protection Corporation, for example. To remove the plug, the intersection of the inlet (or outlet) axis with the body is located. Projecting along this axis, a plug is removed that is approximately equal in diameter to the outside diameter of the inlet (or outlet) to be inserted plus any required tolerances. The plug is made to a depth such that the edge of the inlet (or outlet) liner is aligned with the internal surface of the body liner. FIG. 12 shows a schematic that illustrates a body section liner 1200 having an outside diameter 1202 of 13½ inches (34.29 cm), an inside diameter 1204 of 12 inches (30.48 cm), and a height 1206 of 17½ inches (44.45 cm). The radius 1208 of the cavity 1210 is 4¹³⁄₁₆ inches (12.22 cm) with the distance 1212 from the end 1214 of the body section liner 1200 to the axis 1216 of the cavity 1210 being 5¾ inches (14.61 cm). The distance 1218 from the axis 1216 of the cavity 1210 to the outside edge of the body section liner 1200 is 4¾ inches (12.07 cm).

Figure 13:
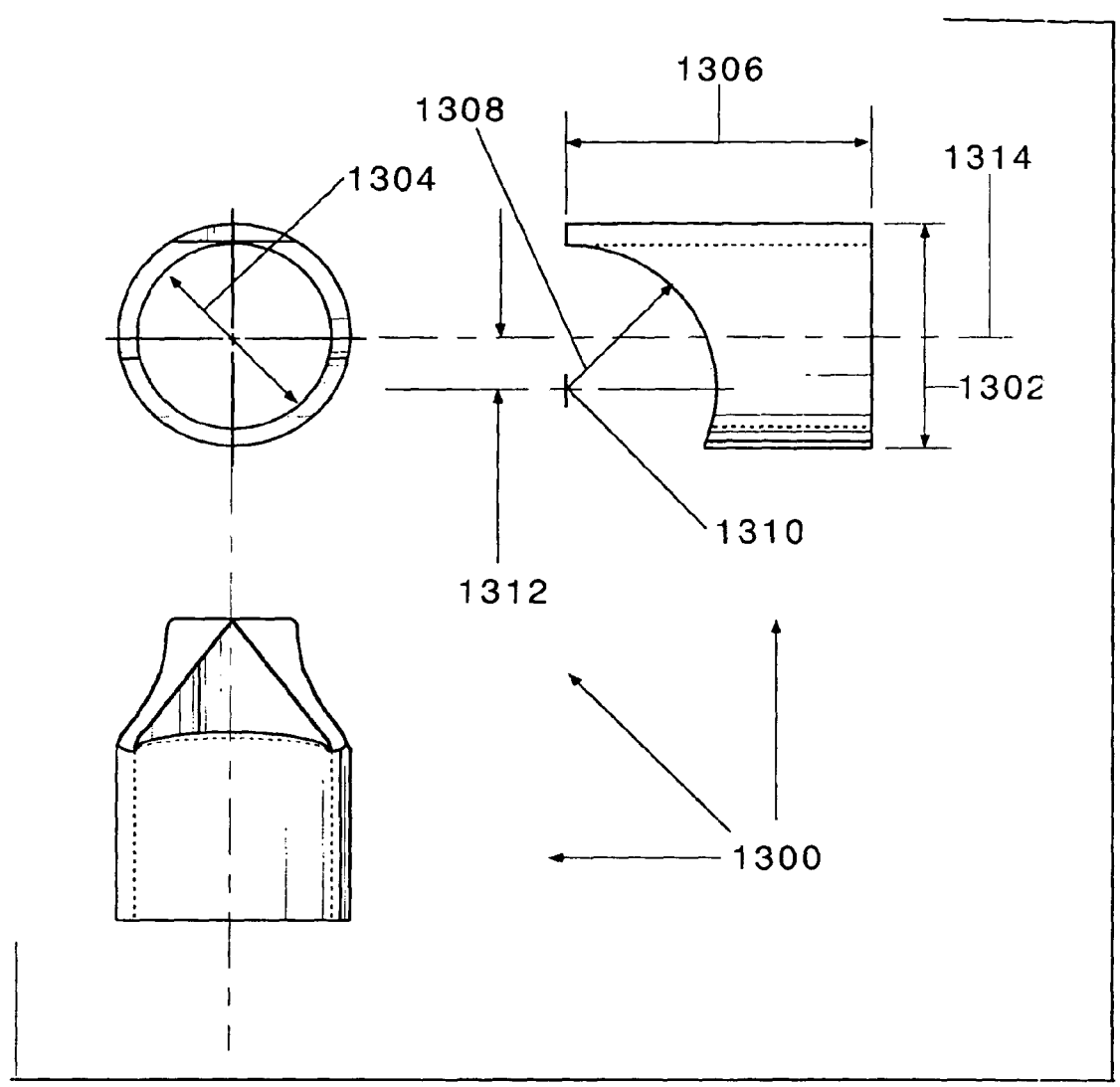
FIG. 13 shows a schematic of the tangential inlet liner of FIG. 11.

Tangential inlet liners and tangential outlet liners also can be created by removing a plug from a cylindrical piece of lining material. The inlet and outlet liners can be created by removing a cylindrical plug having a diameter approximately the same diameter as the inside diameter of the body liner into which the inlet or outlet liner is to be inserted. FIG. 13 shows a schematic that illustrates a tangential inlet (or outlet) liner 1300 having an outside diameter 1302 of 9½ inches (24.13 cm), an inside diameter 1304 of 8 inches (20.32 cm), and a height (or length) 1306 of 12 inches (30.48 cm). As illustrated in FIG. 13, tangential inlet liner 1300 has a cylindrical shape having a height 1306 of 12 inches (30.48 cm) and an outside diameter 1302 of 9½ inches (24.13 cm). The cylindrical shape of tangential inlet liner 1300 has a cylindrical plug removed with a radius 1308 of 6 inches (15.24 cm) removed from the end of the tangential inlet liner 1300. The axis 1310 of the cylindrical plug is a distance 1312 of 2 inches (5.08 cm) from the axis 1314 of the tangential inlet liner 1300 at its closest point. It should be noted that the radius 1308 of the removed cylindrical plug (that is, 6 inches (15.24 cm)) matches the inside diameter 1204 (that is, 12 inches (30.48 cm)) of the body liner 1200.

Liners of the type described herein have several advantages over liners used in the prior art. When refractory brick or tile liner systems are used in process lines or equipment as is known in the art, the liner materials are typically bonded in place by gluing or grouting. Once installed, demolition of the liner system is necessary whenever the liner system must be removed. Bricking and demolition of the liner system are time-consuming and require fresh material to be installed every time. Liners as we have described, on the other hand, allow the liner system in certain applications to be installed and removed repeatedly without damaging the liner materials.

Straight piping lines of the prior art offer the opportunity to insert pre-cast liner sections. However, these liner sections are still usually bonded in place to keep the liner from moving out of position or falling out of the body. Lining a junction such as a tee or a vessel inlet with a vessel body typically requires some type of locating, alignment, or locking method or device. In many cases, this is done by grouting or bonding the parts in place. Once that is done, removal is difficult or impossible without breakage of the liner system. Liners as described herein provide a joint design that aligns and holds the parts of the liner in place with respect to one another, requiring little or no grouting or bonding to maintain the integrity of the joint. That is, once a body liner is inserted into the body of a piping elbow in keeping with FIGS. 8–13, for example, the insertion of a tangential inlet liner and a tangential outlet liner into the cavity of the body liner holds the body liner in place with little or no bonding. Similarly, if the tangential inlet liner and tangential outlet liner are removed, the body liner can be removed for inspection or replacement. In this manner, the tangential inlet liner and the tangential outlet liner are removably inserted into the cavity of the body liner and the body liner is removably inserted into the body of a piping elbow.

Both liners as described and shown herein and liners previously known to the art can be advantageously utilized with various methods according to the present invention, for detecting wear in the liner. Such methods can be extremely important for applications in which the liner contains a flow or movement of abrasive fluids, whether in a vessel, a section of pipe, or a piping elbow of the type described above. One such method utilizes an electrically conductive wire placed on the outside surface of the liner relative to the flowing or moving fluid. The electrical resistance of the wire is periodically measured to determine whether the wire has worn through. If the wire is intact it will have a relatively low electrical resistance. However, if the liner is worn through, the abrasive environment that caused the liner to wear through will, in all likelihood, also cause the wire to wear through and become discontinuous. If the wire is worn through, then the electrical resistance in the wire will be extremely high (essentially infinite). Thus, by measuring the electrical resistance in the electrically conductive wire, one can determine whether the wire, and therefore the liner, has worn through.

The electrically conductive wire can also be placed near the outside surface of the liner to determine when a significant amount of wear has occurred, short of complete wear-through of the liner. In a like manner, a plurality of independent electrically conductive wires could be placed in the liner at varying distances from the abrasive fluid and the resistances of these individually measured to assess wear rate of the liner.

Figure 14:
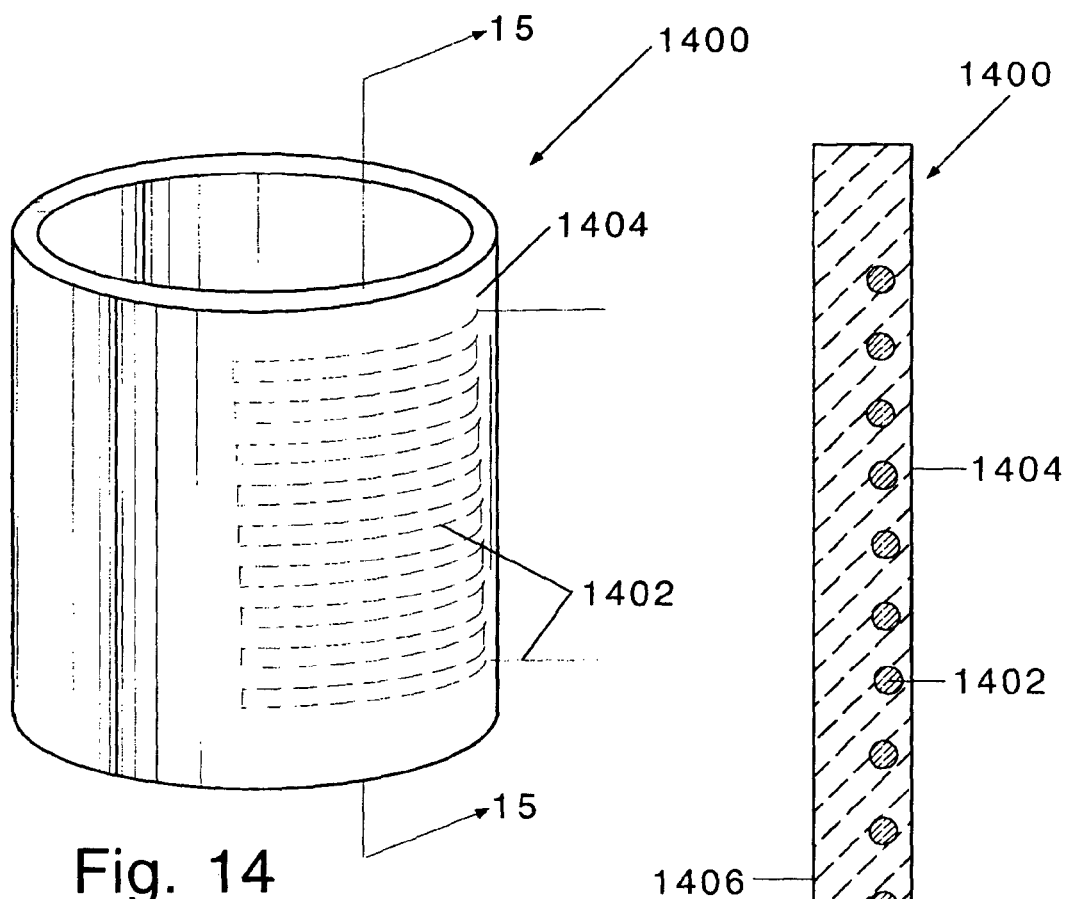
FIG. 14 shows a cylindrically-shaped section of a liner having an electrically conductive wire placed near the outside surface of the liner in a zigzag pattern in accordance with the present invention.
Figure 15:
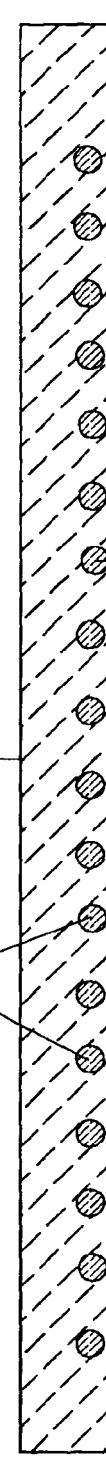
FIG. 15 shows a cross-sectional view of the body section liner shown in FIG. 14

An electrically conductive wire can be placed near the outside surface of a liner, for example, by building the wire into the liner. An example is provided in FIGS. 14 and 15. FIG. 14 shows an electrically conductive wire 1402 placed in a zigzag pattern near the outside surface 1404 of a cylindrically-shaped section of a piping liner 1400. FIG. 15 shows a cross-sectional view of the liner 1400 that illustrates the wire 1402 is placed inside the liner 1400, and therefore, near the outside surface 1404 of the liner 1400. Preferably, the wire 1402 is placed closer to the outside surface 1404 of the liner 1400 than the inside surface 1406 of the liner 1400.

Figures 16, 17:
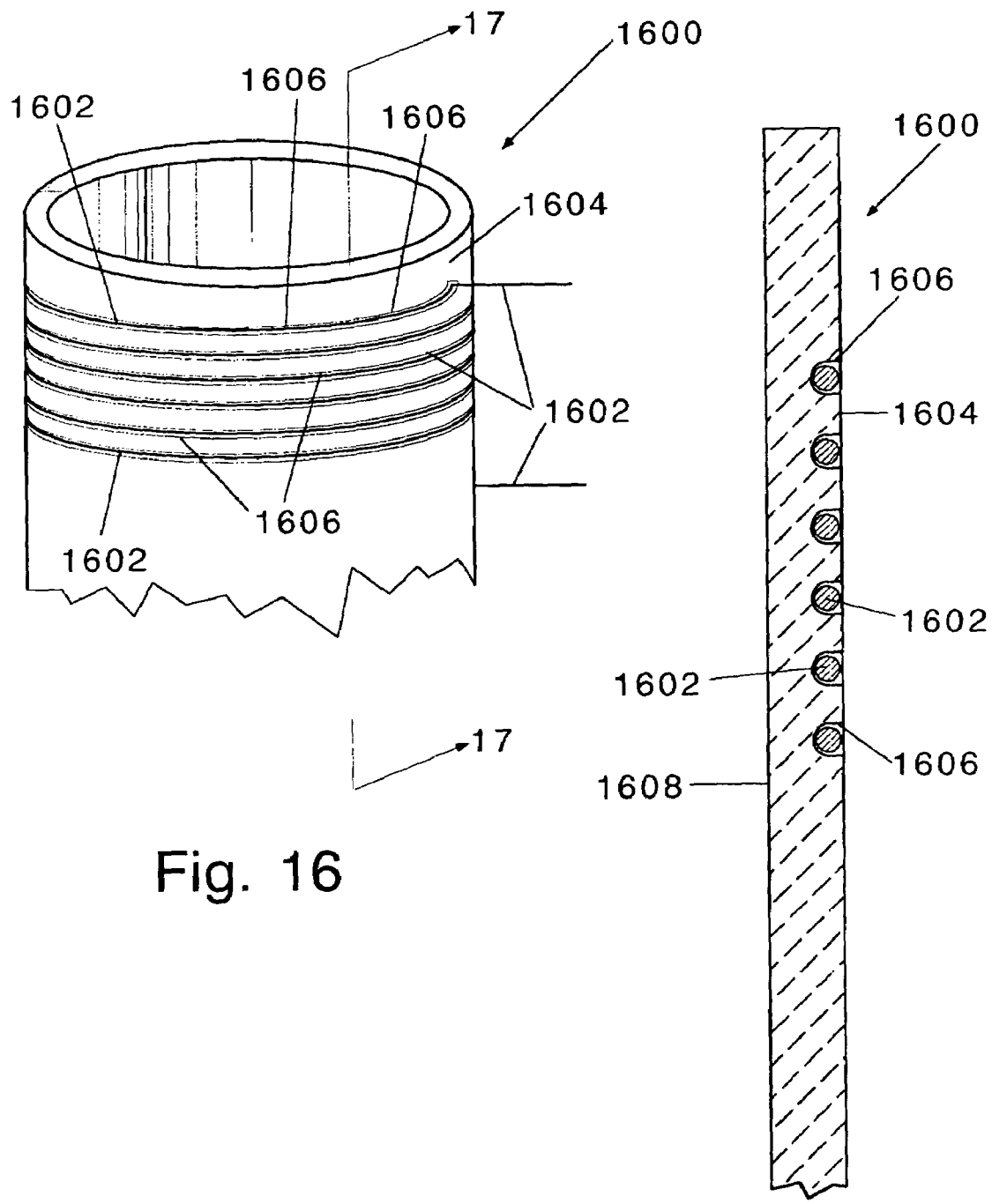
FIG. 16 shows a cylindrically-shaped section of a liner having an electrically conductive wire placed near the outside surface of the liner in a spiral pattern in accordance with the present invention.
FIG. 17 shows a cross-sectional view of the liner section shown in FIG. 16.

FIGS. 16 and 17 illustrate another example of how an electrically conductive wire can be placed near the outside surface of a liner. FIG. 16 shows a cylindrically-shaped section of a piping liner 1600 having an electrically conductive wire 1602 placed near the outside surface 1604 of the liner 1600 in a spiral pattern. The wire 1602 is placed in a groove 1606 that has been created in the outside surface 1604 of the liner. The groove 1606 can be created in any suitable manner. Preferably, the depth of the groove 1606 is chosen such that the electrically conductive wire 1602 is closer to the outside surface 1604 of the liner 1600 than the inside surface 1608 of the liner 1600 when placed in the groove 1606. The groove 1606 in liner 1600 is spiral shaped, but could be any shape suitable for the application, such as a zigzag shape similar to the zigzag pattern shown in FIG. 14. An alternative to the use of electrically conductive wires would be to use temperature measuring devices, for example, a thermocouple, in order to estimate the amount of wear in the liner. For example, if a lined piping construct is used in an application where high-temperature fluids are involved, a temperature measuring device can be advantageously placed on or near the outside surface of the liner. If the liner has heat insulating properties (such as exhibited by a liner made of a ceramic material) then the device over time will detect a gradually increasing temperature as the liner wears away and less insulating liner material separates the temperature measuring device from the high-temperature fluid. Monitoring the temperature detected by the device over time allows the amount of wear on the liner to be estimated. The detected temperature at which a liner is sufficiently worn to be replaced will depend on the temperature of the fluid in contact with the liner, the insulating properties of the liner, and the thickness of the liner material between the temperature measuring device and the fluid. However, a suitable temperature for a given application can be determined without undue experimentation by periodically removing a liner and visually inspecting the amount of wear and noting the temperature detected at the time the liner is removed. Once the wear is sufficient to warrant replacement of the liner, the corresponding temperature can be noted. From that point on, new liners of the same insulating material and thickness can be inserted and not removed until this temperature is detected or closely approached.

In one embodiment of the present invention, a wire thermocouple is advantageously utilized as the temperature measuring device. As is known in the art, a thermocouple can consist of two dissimilar metals joined so that a potential difference generated between the points of contact is a measure of the temperature difference between the points. In a preferred embodiment of the present invention, the wire thermocouple is a type J or K thermocouple. The wire thermocouple can be placed on or near the outside surface of the liner in the same manner that the electrically conductive wire described above is placed and as illustrated in FIGS. 14–17. In another preferred embodiment, the wire thermocouple is also electrically conductive, such that a break in the wire thermocouple can be detected by measuring the electrical resistance of the electrically conductive wire thermocouple in the same manner that the electrical resistance is measured in the electrically conductive wire as described above.

While the present invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and by equivalents thereto.

What is claimed is:

1. A method for detecting wear in a liner containing or bounding a flow of an abrasive fluid, comprising the steps of:
    placing an electrically conductive wire thermocouple on or near the outside surface of the liner;
    measuring the electrical resistance in the wire thermocouple to determine whether the wire has worn through; and
    monitoring the temperature measured by the wire thermocouple over time to estimate wear in the liner.

2. A method according to claim 1, wherein the wire thermocouple is placed in a zigzag pattern.

3. A method according to claim 1, wherein the wire thermocouple is placed in a spiral pattern.

4. A method according to claim 1, wherein the liner is ceramic.

5. A method for detecting wear in a liner containing or bounding a flow of an abrasive fluid, comprising the steps of:
    creating a groove in the outside surface of the liner;

placing an electrically conductive wire thermocouple in the groove;

measuring the electrical resistance in the wire thermocouple to determine whether the wire has worn through; and monitoring the temperature measured by the wire thermocouple over time to estimate wear in the liner.

6. A method according to claim 5, wherein the liner is ceramic.

7. A method according to claim 5, wherein the created groove comprises a zigzag pattern.

8. A method according to claim 5, wherein the created groove comprises a spiral pattern.

* * * * *